(12) United States Patent
Torchia et al.

(10) Patent No.: US 7,691,100 B2
(45) Date of Patent: Apr. 6, 2010

(54) HYPERTHERMIA TREATMENT AND PROBE THEREFOR

(75) Inventors: Mark G. Torchia, Winnipeg (CA); Richard Tyc, Winnipeg (CA); John S. Pacak, Winnipeg (CA)

(73) Assignee: Monteris Medical, Inc., Winnipeg, Manitoba (CA)

( * ) Notice: Subject to any disclaimer, the term of this patent is extended or adjusted under 35 U.S.C. 154(b) by 237 days.

(21) Appl. No.: 11/467,394

(22) Filed: Aug. 25, 2006

(65) Prior Publication Data
US 2006/0287647 A1     Dec. 21, 2006

Related U.S. Application Data

(63) Continuation of application No. 10/014,846, filed on Dec. 14, 2001, now Pat. No. 7,167,741, which is a continuation-in-part of application No. PCT/CA01/00905, filed on Jun. 15, 2001.

(51) Int. Cl.
*A61B 18/04* (2006.01)
(52) U.S. Cl. .............................. 606/27; 606/13; 606/15; 607/89; 607/104; 600/410; 600/411
(58) Field of Classification Search .................. 606/13, 606/15, 20–31; 607/88, 89, 96, 104, 105, 607/107; 600/410–412, 424, 425, 437
See application file for complete search history.

(56) References Cited

U.S. PATENT DOCUMENTS

| | | |
|---|---|---|
| 4,111,209 A | 9/1978 | Wolvek et al. |
| 4,671,254 A | 6/1987 | Fair |

(Continued)

FOREIGN PATENT DOCUMENTS

EP     0610991 A     8/1994

(Continued)

OTHER PUBLICATIONS

Kahn et al—Journal of Computer Assisted Tomography 18(4):519-532—Jul./Aug. 1994 (14 pages).

(Continued)

*Primary Examiner*—Ahmed M Farah
(74) *Attorney, Agent, or Firm*—Barbara A. Wrigley; Oppenheimer Wolff & Donnelly, LLP

(57) ABSTRACT

An MRI guided surgical apparatus includes a heat source formed by a laser and an optical fiber carrying the heat energy into a part to be coagulated by hyperthermia with an end reflector to direct the energy in a beam to one side of the fiber end. A reinforcing sleeve for the fiber is mounted in a shielded, Piezo-electric motor which causes movement of the fiber longitudinally and angularly within a rigid elongate cannula. A magnetic resonance imaging system is arranged to generate a series of output signals over a period of time representative of temperature in the part as the temperature of the part changes during that time. The heat source is controlled in heat energy applied and location and orientation of the beam to stop heating when the temperature at the boundary of a tumor reaches the required hyperthermic temperature. Cooling of the tip portion of the probe is effected by expansion of a supplied cooling fluid in gaseous form through a restrictive orifice into an expansion zone at the probe end. The fiber is thus encased in a stiff tubular titanium probe with a relatively small fluid supply duct along the inside of the probe with the interior of the probe acting as a return duct for the expanded gas. Thus the fiber end is contained in gas rather than liquid and the temperature of the probe end can be monitored by a sensor in the probe end and controlled by controlling the pressure in the supplied cooling fluid. The probe is driven in the longitudinal and rotational directions to move the fiber tip.

20 Claims, 10 Drawing Sheets

U.S. PATENT DOCUMENTS

| | | | |
|---|---|---|---|
| 4,914,608 A | 4/1990 | LeBihan et al. | |
| 5,247,935 A | 9/1993 | Cline et al. | |
| 5,284,144 A | 2/1994 | Delannoy et al. | |
| 5,291,890 A | 3/1994 | Cline et al. | |
| 5,320,617 A | 6/1994 | Leach | |
| 5,327,884 A | 7/1994 | Hardy et al. | |
| 5,366,456 A | 11/1994 | Rink et al. | |
| 5,368,031 A | 11/1994 | Cline et al. | |
| 5,370,649 A | 12/1994 | Gardetto et al. | |
| 5,454,807 A | 10/1995 | Lennox | |
| 5,492,122 A | 2/1996 | Button et al. | |
| 5,537,499 A | 7/1996 | Brekke | |
| 5,620,479 A * | 4/1997 | Diederich | 601/3 |
| 5,672,172 A * | 9/1997 | Zupkas | 606/20 |
| 5,733,277 A | 3/1998 | Pallarito | |
| 5,762,066 A | 6/1998 | Law et al. | |
| 5,785,704 A | 7/1998 | Bille | |
| 5,807,383 A | 9/1998 | Kolesa et al. | |
| 5,823,941 A | 10/1998 | Shaunnessey | |
| 5,861,020 A | 1/1999 | Schwarzmaier | |
| 5,949,929 A | 9/1999 | Hamm | |
| 5,959,246 A | 9/1999 | Gretz | |
| 6,086,532 A | 7/2000 | Panescu et al. | |
| 6,123,719 A | 9/2000 | Masychev | |
| 6,128,522 A | 10/2000 | Acker et al. | |
| 6,246,896 B1 | 6/2001 | Dumoulin et al. | |
| 6,280,384 B1 | 8/2001 | Loeffler | |
| 6,293,282 B1 | 9/2001 | Lemelson | |
| 6,332,891 B1 | 12/2001 | Himes | |
| 6,425,867 B1 | 7/2002 | Vaezy et al. | |
| 6,551,274 B2 | 4/2003 | Heiner | |
| 7,344,529 B2 * | 3/2008 | Torchia et al. | 606/13 |
| 7,479,139 B2 * | 1/2009 | Cytron et al. | 606/21 |
| 2006/0122590 A1 * | 6/2006 | Bliweis et al. | 606/24 |
| 2007/0043342 A1 * | 2/2007 | Kleinberger | 606/21 |

FOREIGN PATENT DOCUMENTS

| | | |
|---|---|---|
| EP | 0614651 | 9/1994 |
| WO | WO 94/04220 A | 3/1994 |
| WO | WO 98/52465 | 11/1998 |
| WO | WO 00/23000 A | 4/2000 |

OTHER PUBLICATIONS

Journal of Magnetic Resonance Imaging JMRI 1998; 8:160-164 (5 pages).

Vogl et al in Radiology 1998; 209 381-385 (5 pages).

H.-J. Schwarzmaier et al. / European Journal of Radiology 59 (2006) 208-215 (8 pages).

Journal of Magnetic Resonance Imaging 22:799-803 (2005) (5 pages).

* cited by examiner

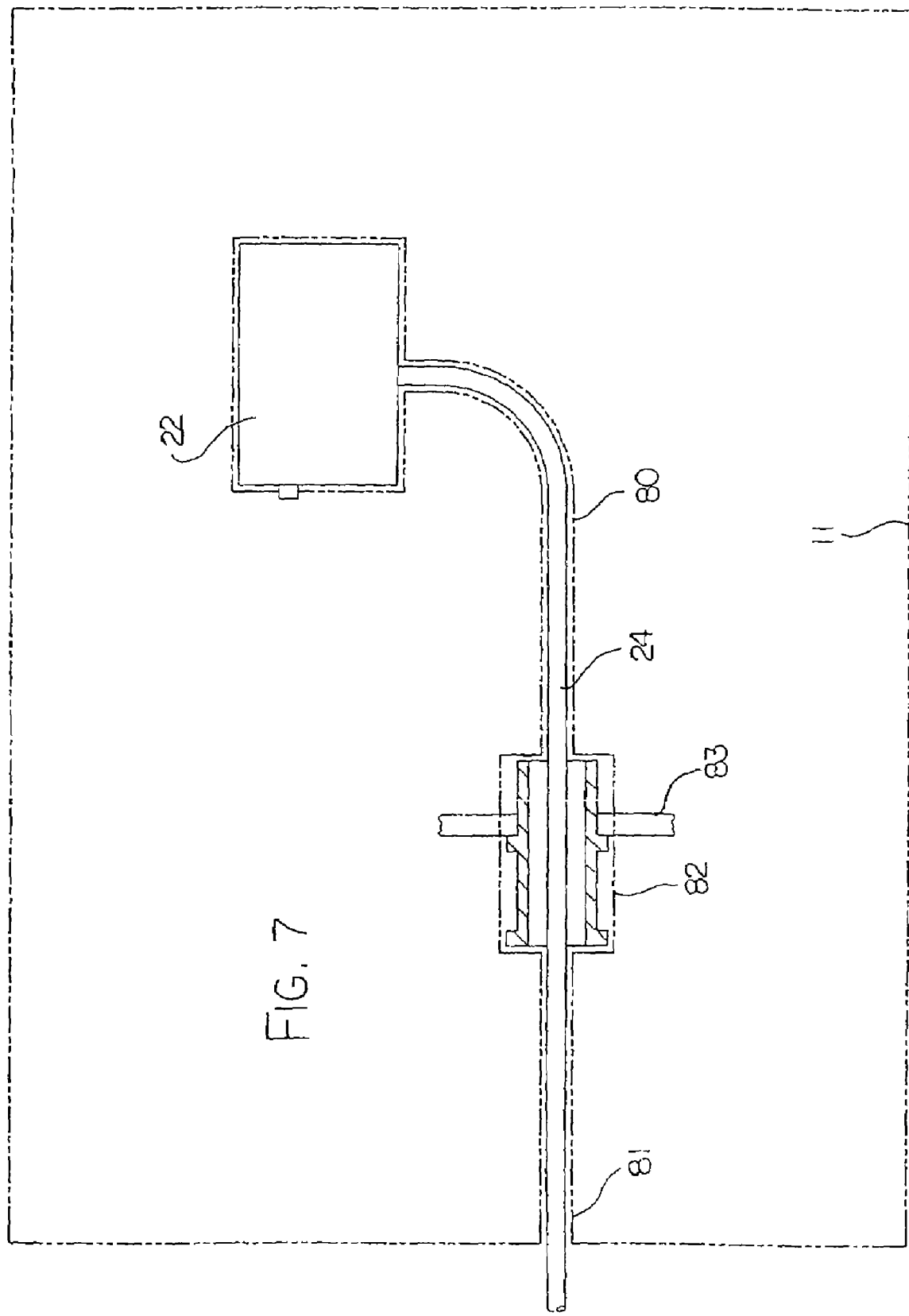

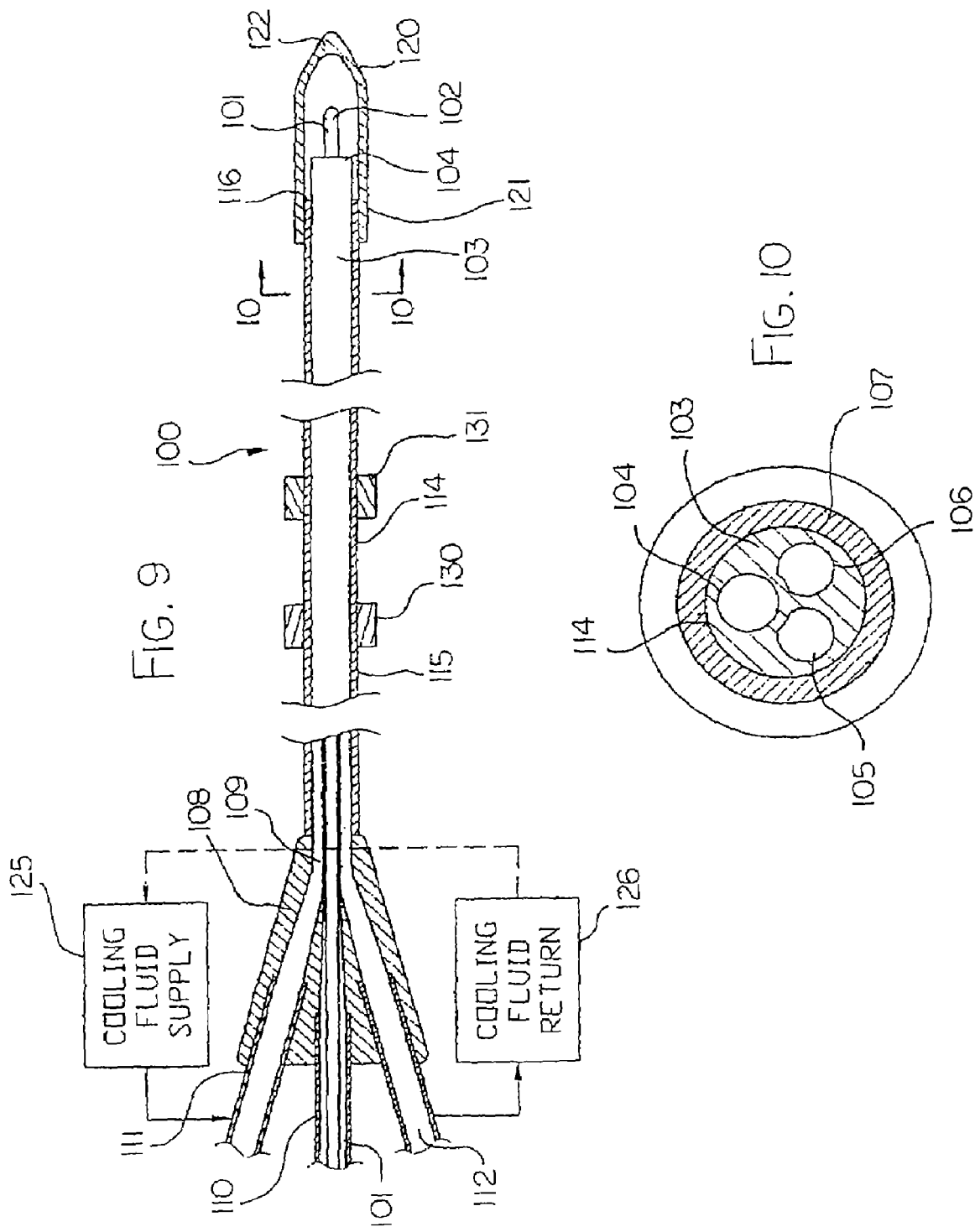

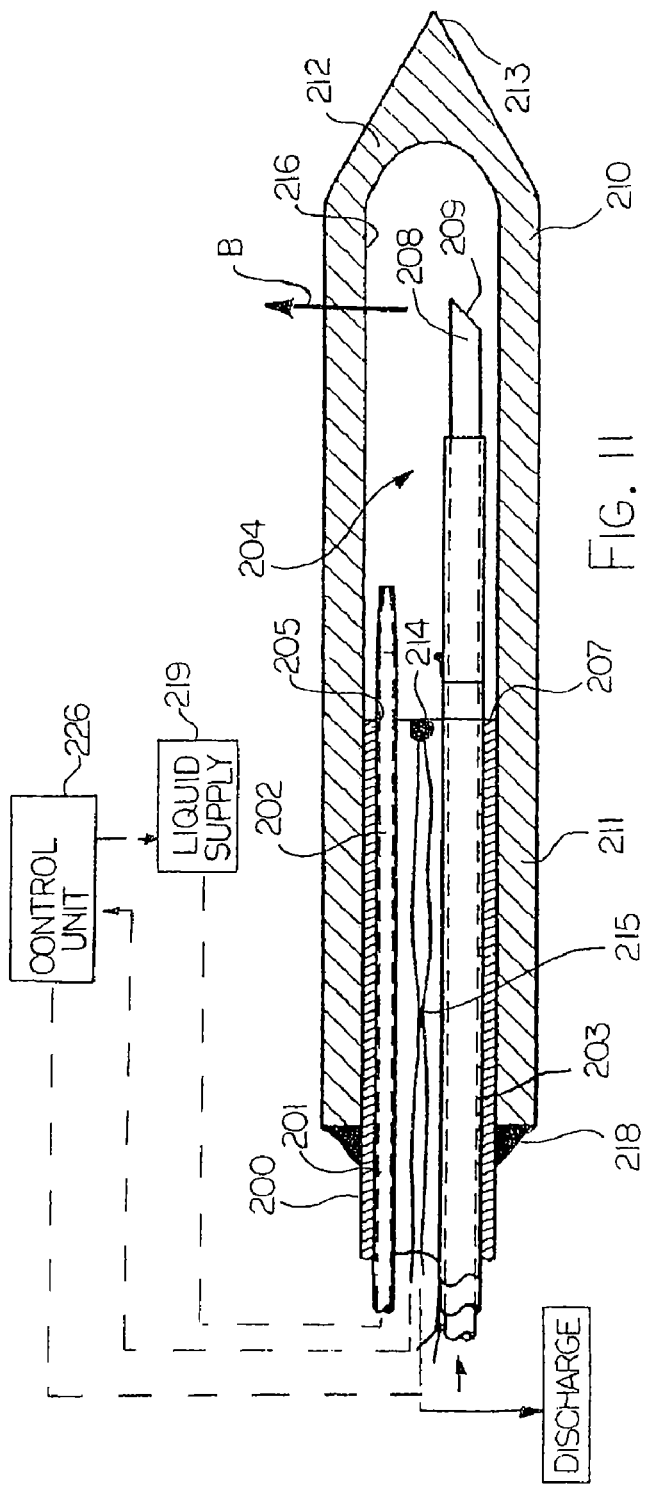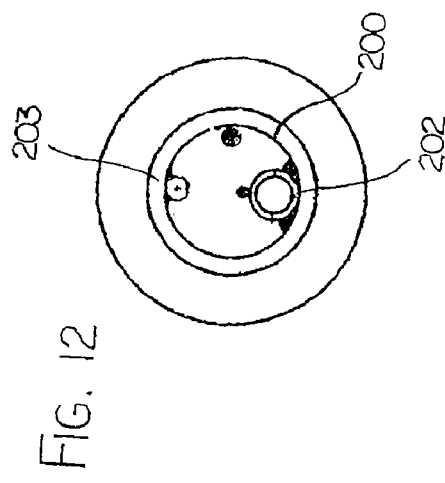
FIG. 11
FIG. 12

HYPERTHERMIA TREATMENT AND PROBE THEREFOR

CROSS REFERENCE TO RELATED APPLICATIONS

This application is a continuation of U.S. application Ser. No. 10/014,846, filed Dec. 14, 2001, now U.S. Pat. No. 7,167, 741, which is a continuation-in-part of PCT Application No. CA01/00905 filed Jun. 15, 2001, which claims priority to U.S. application Ser. No. 09/593,699, filed Jun. 15, 2000, now issued as U.S. Pat. No. 6,418,337, the entireties of which are hereby incorporated by reference.

This invention relates to a method and apparatus for hyperthermia treatment in a patient.

BACKGROUND OF THE INVENTION

The treatment of tumours by hyperthermia is known. Thus tumours and other lesions to be treated can in one known process be heated above a predetermined temperature of the order of 55° C. so as to coagulate the portion of tissue heated. The temperature range is preferably of the order of 55 to 65° C. and does not reach temperatures which can cause carbonization or ablation of the tissue.

One technique for effecting the heating is to insert into the lesion concerned an optical fiber which has at its inserted end an element which redirects laser light from an exterior source in a direction generally at right angles to the length of the fiber. The energy from the laser thus extends into the tissue surrounding the end or tip and effects heating. The energy is directed in a beam confined to a relatively shallow angle so that, as the fiber is rotated, the beam also rotates around the axis of the fiber to effect heating of different parts of the lesion at positions around the fiber. The fiber can thus be moved longitudinally and rotated to effect heating of the lesion over the full volume of the lesion with the intention of heating the lesion to the required temperature without significantly affecting tissue surrounding the lesion.

At this time the fiber is controlled and manipulated by a surgeon with little or no guidance apart from the knowledge of the surgeon of the anatomy of the patient and the location of the lesion. It is difficult therefore for the surgeon to effect a controlled heating which heats all of the lesion while minimizing damage to surrounding tissue.

It is of course well known that the location of tumours and other lesions to be excised can be determined by imaging using a magnetic resonance imaging system. The imaging system thus generates for the surgeon a location of the lesion to be excised but there is no system available which allows the surgeon to use the imaging system to control the heating effect. In most cases it is necessary to remove the patient from the imaging system before the treatment commences and that movement together with the partial excision or coagulation of some of the tissue can significantly change the location of the lesion to be excised thus eliminating any possibility for controlled accuracy.

It is also known that magnetic resonance imaging systems can be used by modification of the imaging sequences to determine the temperature of tissue within the image and to determine changes in that temperature over time.

U.S. Pat. No. 4,914,608 (LeBiahan) assigned to U.S. Department of Health and Human Services issued Apr. 3, 1990 discloses a method for determining temperature in tissue.

U.S. Pat. No. 5,284,144 (Delannoy) also assigned to U.S. Department of Health and Human Services and issued Feb. 8, 1994 discloses an apparatus for hyperthermia treatment of cancer in which an external non-invasive heating system is mounted within the coil of a magnetic resonance imaging system. The disclosure is speculative and relates to initial experimentation concerning the viability of MRI measurement of temperature in conjunction with an external heating system. The disclosure of the patent has not led to a commercially viable hyperthermic treatment system.

U.S. Pat. Nos. 5,368,031 and 5,291,890 assigned to General Electric relate to an MRI controlled heating system in which a point source of heat generates a predetermined heat distribution which is then monitored to ensure that the actual heat distribution follows the predicted heat distribution to obtain an overall heating of the area to be heated. Again this patented arrangement has not led to a commercially viable hyperthermia surgical system.

An earlier U.S. Pat. No. 4,671,254 (Fair) assigned to Memorial Hospital for Cancer and Allied Diseases and issued Jun. 9, 1987 discloses a method for a non surgical treatment of tumours in which the tumour is subjected to shock waves. This does not use a monitoring system to monitor and control the effect.

U.S. Pat. No. 5,823,941 (Shaunnessey) not assigned issued Oct. 20, 1998 discloses a specially modified endoscope which designed to support an optical fiber which emits light energy and is moved longitudinally and rotates angularly about its axis to direct the energy. The device is used for excising tumors and the energy is arranged to be sufficient to effect vaporization of the tissue to be excised with the gas thus formed being removed by suction through the endoscope. An image of the tumor is obtained by MRI and this is used to program a path of movement of the fiber to be taken during the operation. There is no feedback during the procedure to control the movement and the operation is wholly dependent upon the initial analysis. This arrangement has not achieved commercial or medical success.

U.S. Pat. No. 5,454,807 (Lennox) assigned to Boston Scientific Corporation issued Oct. 3, 1995 discloses a device for use in irradiating a tumor with light energy from an optical fiber in which in conjunction with a cooling fluid which is supplied through a conduit with the fiber to apply surface cooling and prevent surface damage while allowing increased levels of energy to be applied to deeper tissues. This arrangement however provides no feedback control of the heating effect.

U.S. Pat. No. 5,785,704 (Bille) assigned to MRC Systems GmbH issued Jul. 28, 1996 discloses a particular arrangement of laser beam and lens for use in irradiation of brain tumors but does not disclose methods of feedback control of the energy. This arrangement uses high speed pulsed laser energy for a photo-disruption effect.

Kahn et al in Journal of Computer Assisted Tomography 18(4):519-532 July/August 1994 and in Journal of Magnetic Resonance Imaging JMRI 1998; 8: 160-164 Vogl et al in Radiology 1998; 209: 381-385 all disclose a method of application of heat energy from a laser through a fiber to a tumor where the temperature at the periphery of the tumor is monitored during the application of the energy by MRI. However none of these papers describes an arrangement in which the energy is controlled by feedback from the monitoring arrangement. The paper of Vogl also discloses a cooling system supplied commercially by Somatex of Berlin Germany for cooling the tissues at the probe end. The system is formed by an inner tube through which the fiber passes mounted within an outer tube arrangement in which cooling fluid is passed between the two tubes and inside the inner tube in a continuous stream.

BRIEF SUMMARY OF THE INVENTION

It is one object of the present invention, therefore, to provide an improved method and apparatus for effecting treatment of a patient by hyperthermia.

According to a first aspect of the invention there is provided a method for effecting treatment in a patient comprising:

identifying a volume in the patient the whole of which volume is to be heated to a required temperature, the volume being defined by a peripheral surface of the volume;

providing a heat source and applying heat to the volume within the patient by;

providing the heat source on an invasive probe having a longitudinal axis and an end;

inserting the end of the probe into the volume;

arranging the probe to cause directing of heat from the end in a direction at an angle to the longitudinal axis such that a heating effect of the probe lies in a disk surrounding the axis;

arranging the direction of the heat so as to define a heating zone which forms a limited angular orientation of heating within the disk such that, as the probe is rotated, the probe causes heating of different angular segments of the volume within the disk;

with the probe at a fixed axial position, rotating the probe about the axis so that the heating zone lies in a selected segment;

wherein the application of heat by the probe to the selected segment causes heat to be transferred from the segment into parts of the volume outside the segment surrounding the end of the probe;

and applying cooling to the end of the probe so as to extract heat from the parts surrounding the probe by conduction of heat therefrom.

Preferably the amount of cooling to the probe is arranged relative to the heating such that the parts of the volume surrounding the end of the probe are cooled sufficiently to cause a net heating effect by which substantially only the segment of the heating zone is heated to the required temperature and the parts outside the segment are not heated to the required temperature. This is preferably arranged so that the cooling maintains the parts outside the segment below a temperature sufficient to cause coagulation of the tissues therein. Thus when the probe is rotated to take up a new angle within a new segment, the tissue in the new segment is not in a condition by pre-heating which would interfere with the transmission and diffusion of the heat to that segment.

The arrangement of the present invention, that is the method defined above or the method or probe defined hereinafter, can be used on a rigid probe which is intended to be inserted in a straight line into a specific location in the body of the patient, or can be used on a flexible probe which can be guided in movement through a part of the body such as a vein or artery to a required location.

While the most likely and currently most suitable energy source is that of laser light, the arrangements described and defined herein can also be used with other energy sources of the type which can be directed to one side of the channel through which they are supplied such as electron beams or ultrasound generators.

In one preferred arrangement, the above method can be used with MRI real time control of the surgery by which a non-invasive detection system, such as MRI, is operated to generate a series of output signals over a period of time representative of temperature in the patient as the temperature of the patient changes during that time. The output signals are used to monitor at least one temperature of the volume as the temperature changes over the period of time. The application of heat to the probe is then controlled in response to the changes in temperature wherein the temperature at the peripheral surface of the volume is monitored and a measure of the temperature at a location on the peripheral surface of the volume is used as the determining factor as to when to halt heating by the probe to the location. However the cooling effect can be used without the MRI monitoring to provide an enhanced system in which the whole of the volume required can be heated to the required temperature.

In the method in which temperature is monitored, the determination as to when to halt heating by the probe to the location is made based upon the temperature at the peripheral surface of the volume, with the exception that temperatures within the volume may be monitored to ensure that no serious or dangerous over-temperature occurs within the volume due to unexpected or unusual conditions. Thus any such over-temperature may be detected and used to halt further treatment or to trigger an alarm to the doctor for analysis of the conditions to be undertaken.

When used as a rigid probe for treatment within a body part such as the brain or liver, the probe itself may be sufficiently rigid and strong to accommodate the forces involved or there may be provided a cannula through which the probe is inserted, the cannula having an end which is moved to a position immediately adjacent but outside the volume and the probe having a rigid end portion projecting from the end of the cannula into the volume.

In the preferred arrangement, the heat source comprises a laser, an optical fiber for communicating light from the laser and a light directing element at an end of the fiber for directing the light from the laser to the predetermined direction relative to the fiber forming the limited angular orientation within the disk.

In accordance with a particularly preferred arrangement which provides the necessary level of cooling in a readily controllable process, the end of the probe is cooled by:

providing on the probe a supply duct for a cooling fluid extending from a supply to the end of the probe;

providing an expansion zone of reduced pressure at the end of the probe so as to cause the cooling fluid to expand as a gas thus generating a cooling effect;

and providing on the probe a return duct for return of the expanded gas from the end of the probe.

In this arrangement, the return duct is preferably of larger cross-sectional area than the supply duct and the supply duct includes a restricting orifice at its end where the return duct is larger in cross-sectional area by a factor of the order of 200 times larger than the orifice of the supply duct.

Preferably where the probe comprises a tube the supply duct is arranged inside the tube and the return duct is defined by an inside surface of the tube.

In this arrangement, the supply duct is attached as tube to an inside surface of the tube and the fiber itself is attached also to the inside.

In this arrangement, the orifice is provided by a restricting valve or neck in the supply duct immediately upstream of the expansion chamber at the end of the probe.

Where the fiber has a chamfered end of the fiber it may include a reflecting coating thereon for directing the light energy to the side. The arrangement of the chamfered end can have the advantage or feature that the chamfered end is located in the gas rather than being wetted by cooling fluid which can, when there is no coating, interfere with the reflective properties of the coating and thus with the proper control and direction of the light.

In this arrangement, the chamfered end can be arranged directly at 45 degrees to provide a light direction lying wholly in a radial plane at right angles to the axis of the fiber. The chamfered end may carry a coating arranged to reflect light at two different wavelengths.

In order to accurately control the cooling effect to maintain the net heating required, there is preferably provided a temperature sensor at the end of the probe, which may be located inside the tube with the connection therefor passing through the probe to the control system outside the probe.

Preferably the temperature at the end of the probe is controlled by varying the pressure in the fluid as supplied through the supply duct. This system can allow the temperature to be maintained between about zero and minus 20 degrees Celsius which provides the required level of cooling to the probe for the net heating effect.

According to a second aspect of the invention there is provided a method for effecting treatment in a patient comprising:

identifying a volume in the patient to be heated to a required temperature;

providing a heat source for applying heat to the volume within the patient, providing a probe mounting the heat source allowing invasive insertion of an end of the probe into the patient, providing a position control system for moving the end of the probe to a required position within the patient;

inserting the end of the probe into the volume;

providing on the probe a supply duct for a cooling fluid extending from a supply to the end of the probe;

providing an expansion zone of reduced pressure at the end of the probe so as to cause the cooling fluid to expand as a gas thus generating a cooling effect;

and providing on the probe a return duct for return of the expanded gas from the end of the probe.

According to a third aspect of the invention there is provided a probe for use in effecting treatment in a patient comprising:

a heat source for applying heat to a volume within the patient, a probe body mounting the heat source thereon for allowing invasive insertion of an end of the probe into the patient, a supply duct on the probe body for a cooling fluid extending from a supply to the end of the probe;

the probe body being arranged to provide an expansion zone of reduced pressure at the end of the probe body so as to cause the cooling fluid to expand as a gas thus generating a cooling effect;

and a return duct on the probe body for return of the expanded gas from the end of the probe.

BRIEF DESCRIPTION OF THE DRAWINGS

One embodiment of the invention will now be described in conjunction with the accompanying drawings in which:

FIG. 7 is a schematic illustration of the shielding of the apparatus of FIG. 1.

FIG. 9 is a longitudinal cross sectional view through an alternative form of probe which provides a flow of cooling fluid to the end of the probe for cooling the surrounding tissue.

FIG. 10 is a cross sectional view along the lines 10-10 of FIG. 9.

FIG. 11 is a longitudinal cross sectional view through a further alternative form of probe which provides a flow of cooling fluid to the end of the probe for cooling the surrounding tissue.

FIG. 12 is a cross sectional view along the lines 12-12 of FIG. 11.

DETAILED DESCRIPTION OF THE INVENTION

Figure 1:
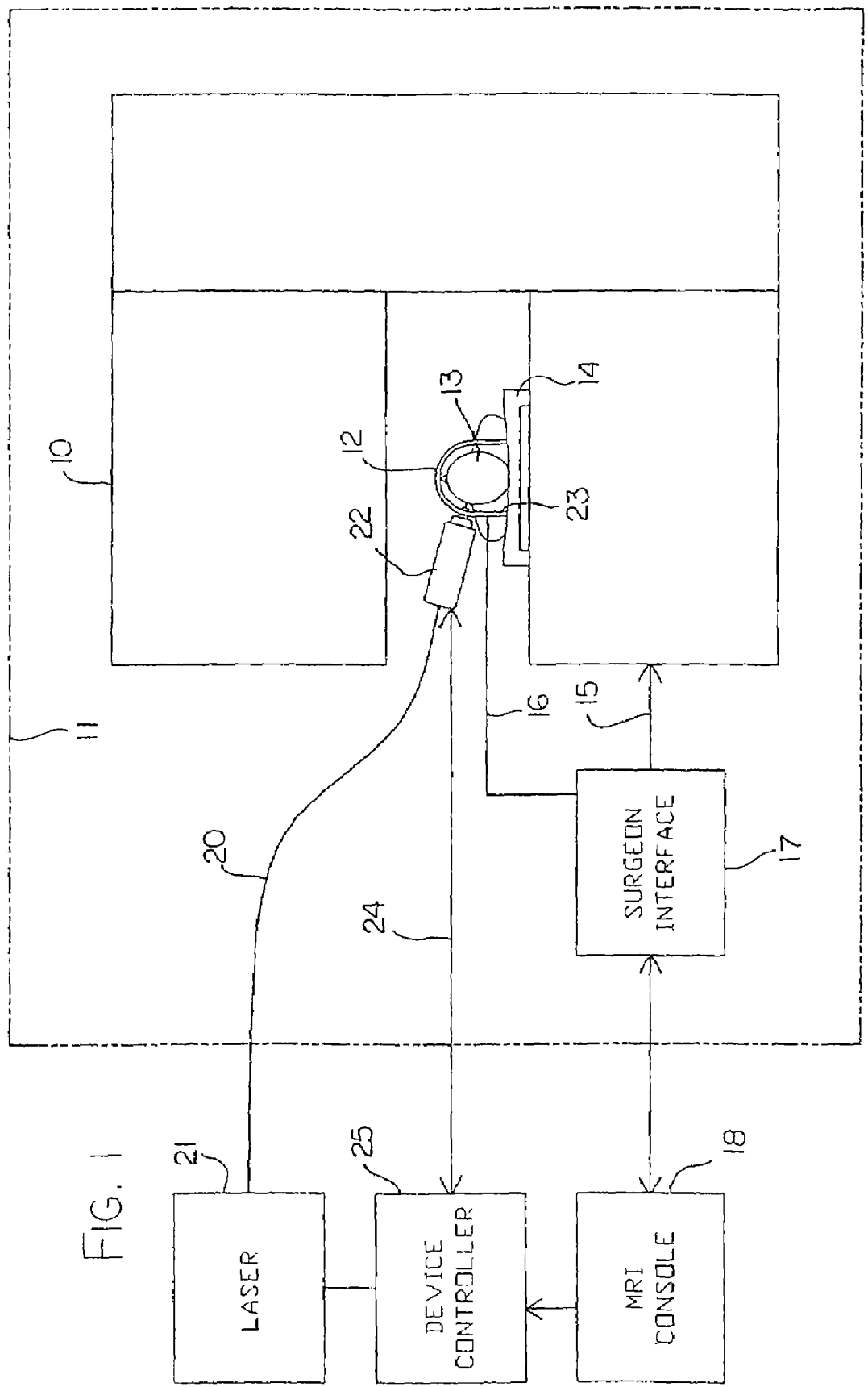
FIG. 1 is a schematic illustration of an apparatus for effecting MRI guided laser treatment according to the present invention.

In FIG. 1 is shown schematically an apparatus for carrying out MRI controlled laser treatment. The apparatus comprises a magnetic resonance imaging system including a magnet 10 provided within a shielded room 11. The magnet 10 can be of any suitable construction and many different magnet arrangements are available from different manufacturers. The magnet includes field coils for generating variations in the magnetic field which are not shown since these are well known to one skilled in the art together with a radio frequency antenna coil which receives signals from the sample in this case indicated as a human patient 13.

The patient 13 rests upon a patient support table 14 on which the patient is supported and constrained against movement for the operative procedure. The fields of the magnet are controlled on an input control line 15 and the output from the antenna coil is provided on an output line 16 both of which communicate through a surgeon interface 17 to the conventional MRI control console 18. The MRI console and the magnet are shown only schematically since these are well known to one skilled in the art and available from a number of different manufacturers.

The apparatus further includes a laser treatment system including an optical fiber 20 which transmits heat energy in the form of light from a laser 21 mounted outside the room 11. The fiber extends into the room to a tip 21 (FIG. 2) at which the energy escapes into the relevant part of the patient as discussed hereinafter. The position of the fiber 20 within the patient and the orientation of the fiber is controlled by a drive motor 22 supported in fixed adjustable position on a stereotaxic frame 23. The motor communicates through a control line 24 to a device controller 25. In general the device controller receives information from the MRI console and from position detectors of the motor 22 so as to operate movement of the motor 22 and to operate a power output from the laser 21 so as to control the position and amount of heat energy applied to the part within the body of the patient.

Figure 2:
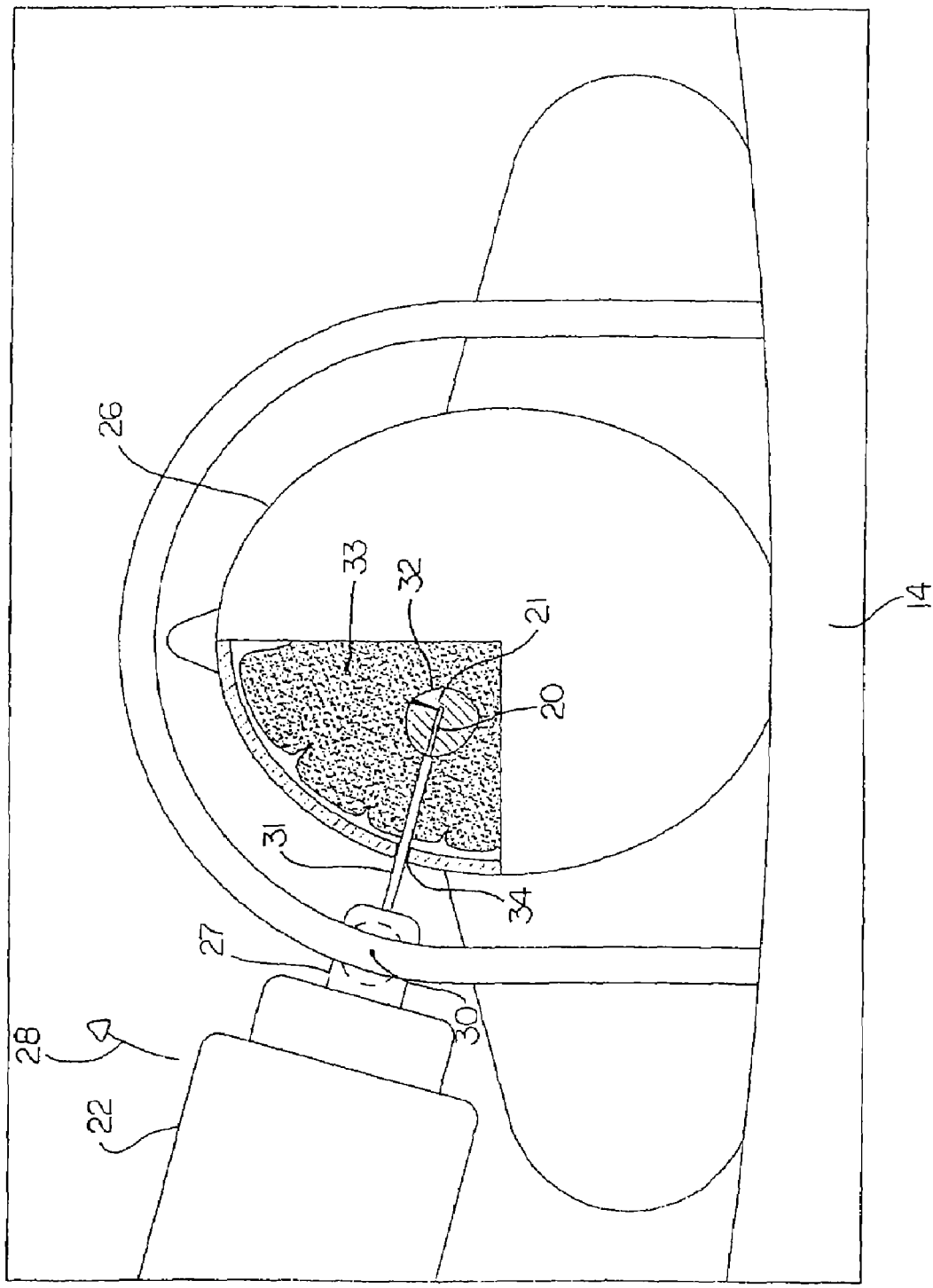
FIG. 2 is a schematic illustration of the apparatus of FIG. 1 on an enlarged scale and showing the emission of laser energy into the brain of a patient.

In FIG. 2 is shown on a larger scale the patient table 14 to which is attached the stereotaxic frame 23 so that the frame is fixed relative to the table and extends over the head 26 of the patient. The frame is shown schematically and suitable details will be well known to one skilled in the art, but carries the motor 22 in a position on the frame by a bracket 27 of the motor. The position of the motor on the frame remains fixed during the procedure but can be adjusted in the arcuate direction 28 around the arch of the frame 23. The frame 23 can also be adjusted forwardly and rearwardly on the table 14. The bracket 27 also allows rotation of the motor about a point 30 within the frame so that the direction of the fiber projecting forwardly from the motor can be changed relative to the frame.

The apparatus further includes a rigid cannula 31 which surrounds the fiber 20 and which is arranged to allow sliding movement of the fiber longitudinally in the cannula and rotational movement within the cannula while generally holding the fiber in a direction axial of the cannula. The cannula is formed of a suitable rigid MRI compatible material such as ceramic so that it is stiff and resistant to bending and has sufficient strength to allow the surgeon to insert the cannula into the required location within the body part of the patient.

In the arrangement as shown, the apparatus is arranged for operating upon a tumour 32 within the brain 33 of the patient. The surgeon therefore creates an opening 34 in the skull of the patient and directs the cannula 31, in the absence of the fiber 20, through the opening 34 to the front edge of the tumour 32.

The position of the tumour is determined in an initial set of MRI experiments using conventional surgical and an analytical techniques to define the boundaries, that is a closed surface within the volume of the brain which constitutes the extremities of the tumour. The surgical analysis by which the surgeon determines exactly which portions of the material of the patient should be removed is not a part of this invention except to say that conventional surgical techniques are available to one skilled in the art to enable an analysis to be carried out to define the closed surface.

The angle of insertion of the cannula is arranged so that, of course, it avoids as far as possible areas of the patient which should not be penetrated such as major blood vessels and also so that the cannula is directed so that, when it reaches the outside surface, it points toward a center of the tumour.

Figure 3:
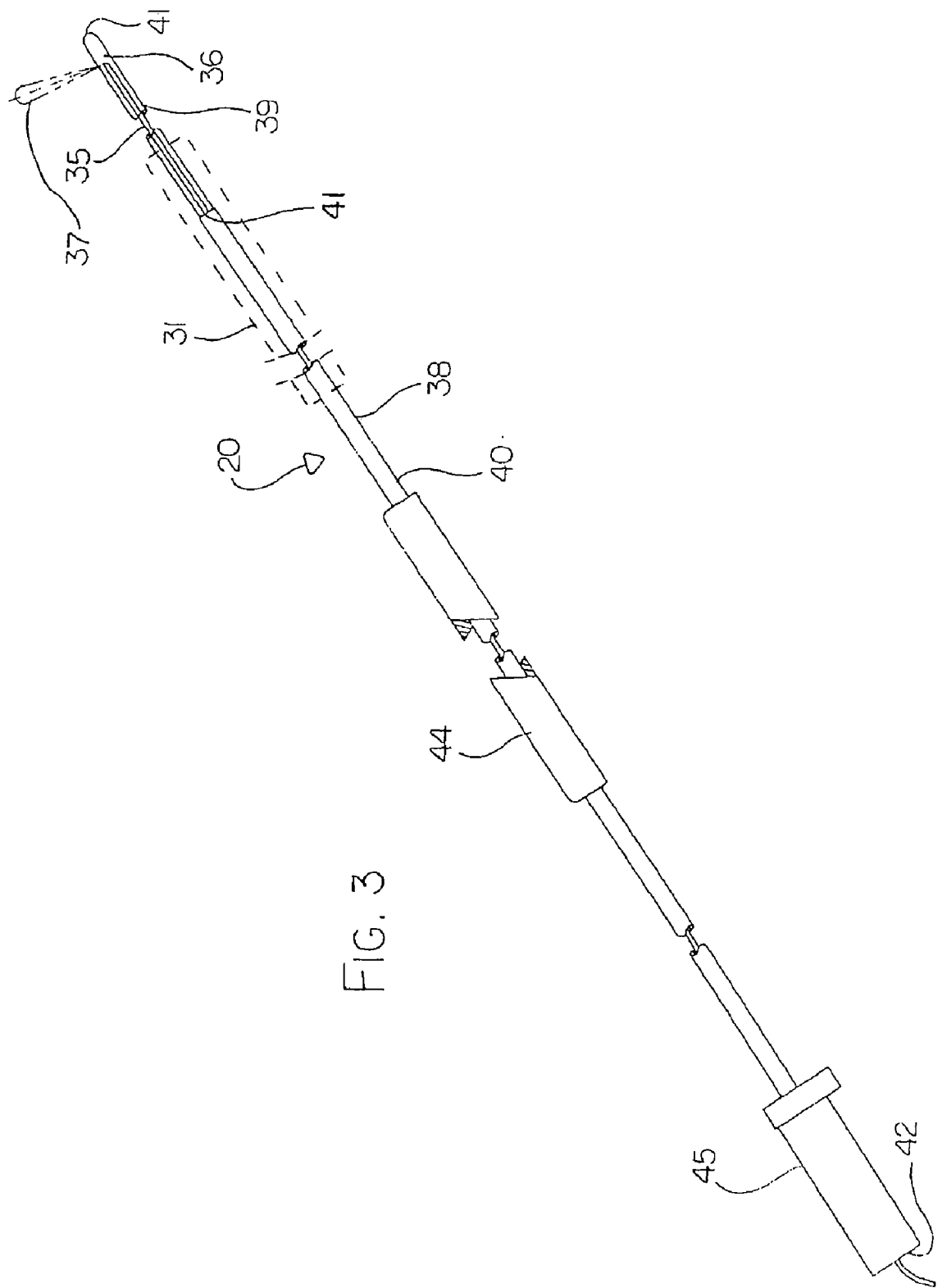
FIG. 3 is a side elevational view of the laser probe of the apparatus of FIG. 1.

The optical fiber structure generally indicated at 20 in FIG. 3 includes an actual glass fiber element 35 which has an inlet end (not shown) at the laser and a remote end 36. At the remote end is provided a reflector or prism which directs the laser energy in a beam 37 to one side of the end 36. Thus the beam 37 is directed substantially at right angles to the length of the fiber and over a small angle around the axis of the fiber. The beam 37 forms a cone having a cone angle of the order of 12 to 15 degrees. Such fibers are commercially available including the reflector or prism for directing the light at right angles to the length of the fiber.

The fiber element itself as indicated at 35 is however encased in an enclosure to allow the fiber to be manipulated in the motor 22. Around the fiber is formed a sleeve 38 including a first end portion 39 and a second longer portion 40. The end portion 39 encloses the end 36 which is spaced from a tip 41 of the end portion. The end portion extends over the length of the order of 7 to 11 cm. The longer second portion 38 is of the order of 48 to 77 cm in length and extends from a forward end 41 through to a rear end 42. The front portion 39 is formed of a rigid material such as glass. The longer rear portion 40 is formed of a stiff material which is less brittle than glass and yet maintains bending and torsional stiffness of the fiber so that forces can be applied to the sleeve portion 40 to move the tip 36 of the fiber to a required position within the tumour. The second portion 40 is formed of a material such as fiber reinforced plastics.

The two portions are bonded together to form an integral structure of common or constant diameter selected as a sliding fit through the cannula. The rigid front portion has a length so that it can extend from the end of the cannula at the forward or closest edge of the tumour through to the rear edge of the tumour. An average tumour might have a diameter of the order of 0.5 to 5.0 cm so that the above length of the forward portion is sufficient to extend through the full diameter of the tumour while leaving a portion of the order of 1.25 cm within the end of the cannula. In this way the substantially rigid forward portion maintains the forward portion of the fiber lying substantially directly along the axis of the cannula without any bending or twisting of the forward portion within the cannula. The longer second portion is not formed from glass since this would provide a complete structure which is too brittle to allow the surgeon to insert the structure into the cannula without the danger of cracking or fracturing the structure under any bending loads. A less brittle material is therefore selected which can accommodate some bending loads caused by manual insertion of the structure into the cannula and yet can communicate the forces from longitudinal and rotational movement as described herein after.

The sleeve portion 40 has attached to it a first polygonal or non-circular section 44 and a second end stop section 45. Both of the drive sections 44 and 45 are connected to the second portion so as to communicate driving action to the second portion. Thus the polygonal section 44 is arranged to co-operate with a drive member which acts to rotate the second portion and therefore the fiber along its full length about an axis longitudinal of the fiber. The second end stop section 45 is arranged to co-operate with a longitudinally movable drive element which moves the second portion and therefore the fiber longitudinally. In this way the tip 36 can be moved from an initial position in which it projects just beyond the outer end of the cannula outwardly into the body of the tumour until the tip reaches the far end of the tumour. In addition the tip can be rotated around the axis of the fiber so that the heat energy can be applied at selected angles around the axis. By selectively controlling the longitudinal movement and rotation of the tip, therefore, the heat energy can be applied throughout a cylindrical volume extending from the end of the cannula along the axis of the cannula away from the end of the cannula. In addition by controlling the amount of heat energy applied at any longitudinal position and angular orientation, the heat energy can be caused to extend to required depths away from the axis of the cannula so as to effect heating of the body part of the patient over a selected volume with the intention of matching the volume of the tumour out to the predetermined closed surface area defining the boundary of the tumour.

Figure 4:
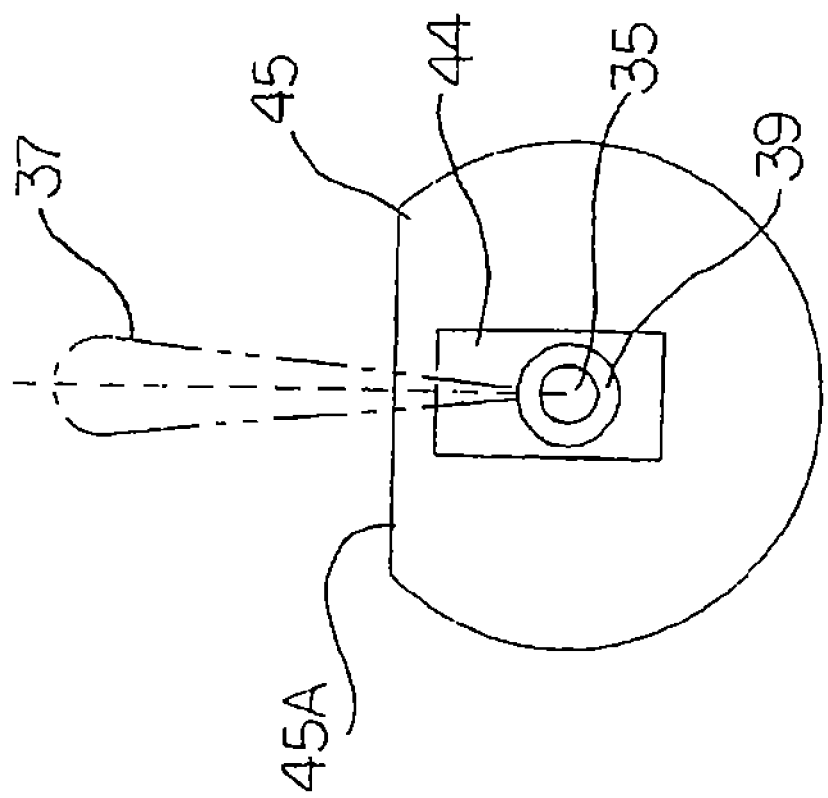
FIG. 4 is an end elevational view of the laser probe of the apparatus of FIG. 1.

As shown in FIG. 4, the non-circular cross section of the drive portion 44 is rectangular with a height greater than the width. However of course other non-circular shapes can be used provided that the cross section is constant along the length of the drive portion and provided that the drive portion can co-operate with a surrounding drive member to receive rotational driving force therefrom. The end stop member 45 is generally cylindrical with a top segment 45A removed to assist the operator in insertion of the fiber into the drive motor.

Figure 5:
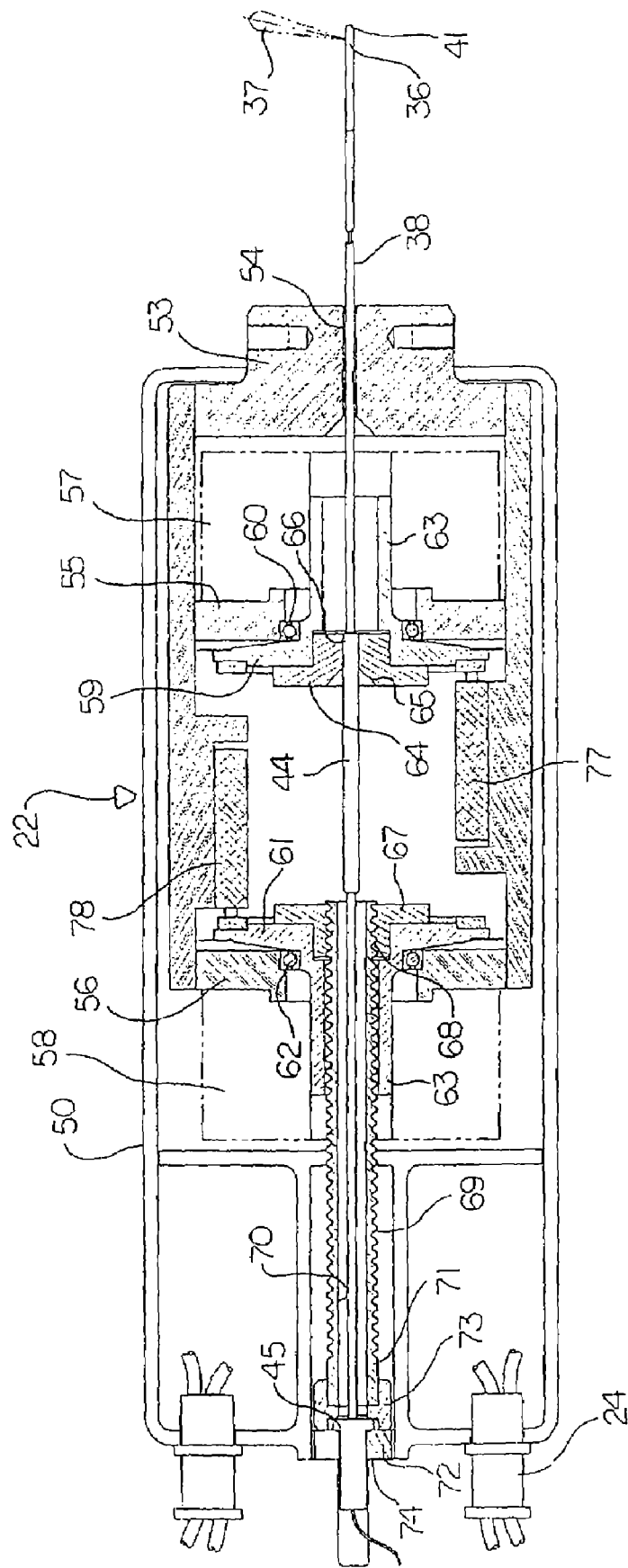
FIG. 5 is a cross sectional view of the laser probe and drive motor therefor of the apparatus of FIG. 1.
Figure 6:
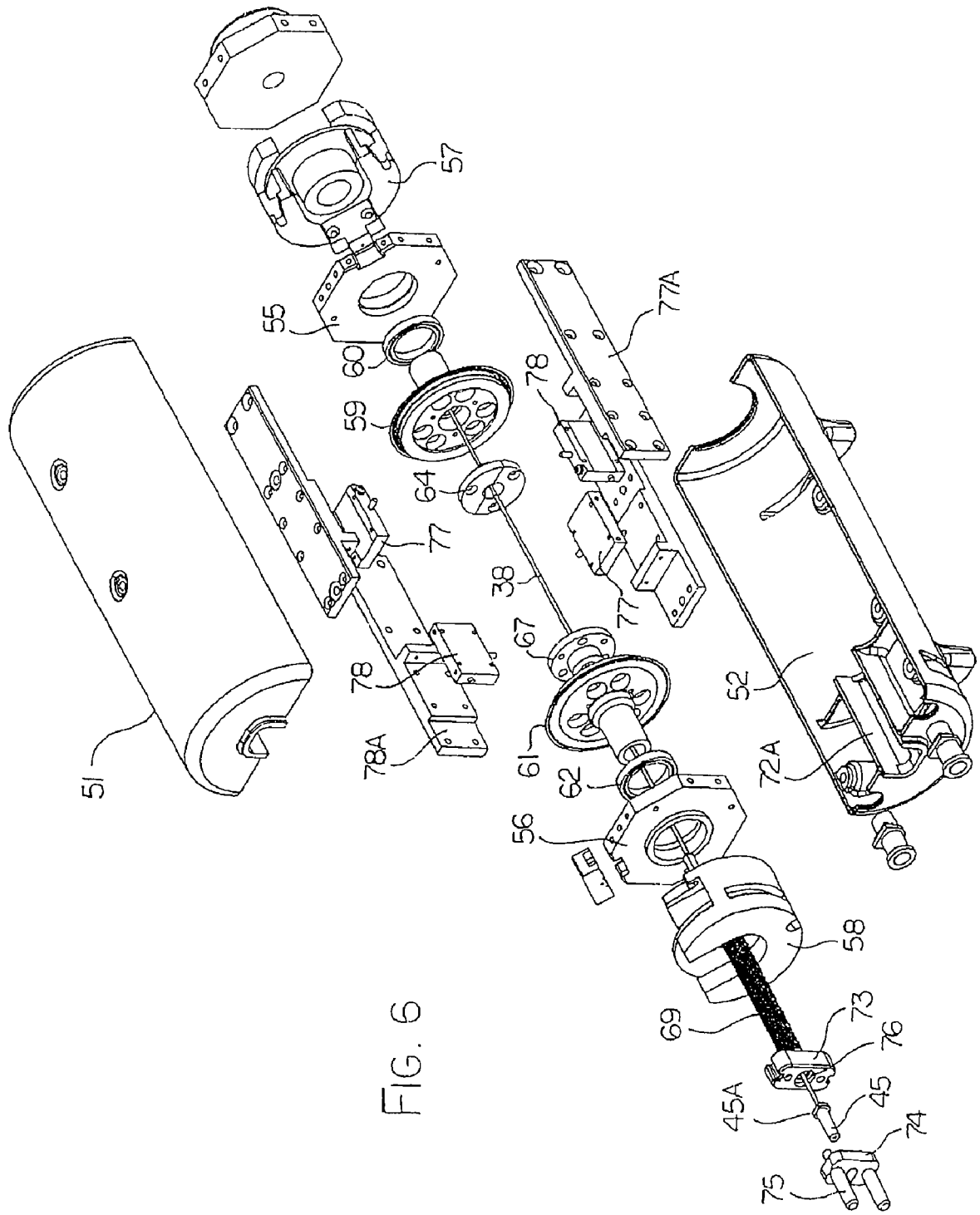
FIG. 6 is an exploded view of the drive motor of the apparatus of FIG. 1.

Turning now to FIGS. 5 and 6, the drive motor 22 is shown in more detail for effecting a driving action on the fiber through the drive members 44 and 45 into the sleeve 38 for driving longitudinal and rotational movement of the tip 36.

The drive motor comprises a housing 50 formed by an upper half 51 and a lower half 52 both of semi-cylindrical shape with the two portions engaged together to surround the drive elements with the fiber extending axially along a center of the housing. At the front 53 of the housing is provided a boss defining a bore 54 within which the sleeve 38 forms a sliding fit. This acts to guide the movement of the sleeve at the forward end of the housing.

Within the housing is provided a first annular mount 55 and a second annular mount 56 spaced rearwardly from the first.

Between the first annular mount and the front boss is provided a first encoder 57 and behind the second annular mount 56 is provided a second encoder 58.

The first annular mount 55 mounts a first rotatable drive disk 59 on bearings 60. The second annular mount carries a second drive disk 61 on bearings 62. Each of the drive disks is of the same shape including a generally flat disk portion with a cylindrical portion 63 on the rear of the disk and lying on a common axis with the disk portion. The bearings are mounted between a cylindrical inner face of the annular portion 55, 56 and an outside surface of the cylindrical portions 63. Each of the disks is therefore mounted for rotation about the axis of the fiber along the axis of the housing.

The disk 59 includes a central plug portion 64 which closes the center hole of the disk portion and projects into the cylindrical portion 63. The plug portion has a chamfered or frusto-conical lead in section 65 converging to a drive surface 66 surrounding the drive member 44 and having a common cross sectional shape therewith. Thus the tip portion 41 of the sleeve 38 can slide along the axis of the housing and engage into the conical lead in section 65 so as to pass through the drive surface or bore 66 until the drive member 44 engages into the surface 66. In the position, rotation of the disk 59 drives rotation of the sleeve 38 and therefore of the fiber. As the drive portion 44 has a constant cross section, it can slide through the drive surface 66 forwardly and rearwardly.

The disk 61 includes a plug member 67 which engages into the central opening in the disk member 61. The plug 67 has an inner surface 68 which defines a female screw thread for co-operating with a lead screw 69. The lead screw 69 has an inner bore 70 surrounding the sleeve 38 so that the sleeve 38 is free to rotate and move relative to the bore 70. The lead screw 69 also passes through the cylindrical portion 63 of the disk 61. However rotation of the disk 61 acts to drive the lead screw longitudinally of the axis of the housing and therefore of the axis of the sleeve 38. A rear end 71 of the lead screw is attached to a clamping member 72. The clamping member 72 includes a first fixed portion 73 attached to the rear end 71 of the lead screw and a second loose portion 74 which can be clamped into engaging the fixed portion so as to clamp the end stop members 45 in position within the clamping member. The loose portion 74 is clamped in place by screws 75. The top segment 45A of the end stop 45 engages into a receptacle 76 in the fixed portion 73 so as to orient the sleeve 38 relative to the lead screw.

The disks 59 and 61 are driven in a ratchetting action by drive motors 77 and 78 respectively. In the preferred embodiment the drive motors are provided by piezo-electric drive elements in which a piezo-electric crystal is caused to oscillate thus actuating a reciprocating action which is used to drive by a ratchet process angular rotation of the respective disk.

The reciprocating action of the piezo-electric crystal 77 and 78 is provided by two such motors 77 co-operating with the disk 59 and two motors 78 co-operating with the disk 61. Each motor is carried on a mounting bracket 77A, 78A which is suitably attached to the housing.

The end clamp 72 is generally rectangular in cross section and slides within a correspondingly rectangular cross section duct 72A within the housing. Thus the lead screw 69 is held against rotation and is driven axially by the rotation of the disk 61 while the fiber is free to rotate relative to the lead screw.

In other alternative arrangements (not shown), the ratchetting action can be effected by a longitudinally moveable cable driven from the device controller 25 outside the room 11. In a further alternative arrangement, the motor may comprise a hydraulic or pneumatic motor which again effects a ratcheting action by reciprocating movement of a pneumatically or hydraulically driven prime mover.

Thus selected rotation of a respective one of the disks can be effected by supplying suitable motive power to the respective motor.

The respective encoder 57, 58 detects the instantaneous position of the disk and particularly the sleeve portion 63 of the disk which projects into the interior of the encoder. The sleeve portion therefore carries a suitable elements which allows the encoder to detect accurately the angular orientation of the respective disk. In this way the position of the disks can be controlled by the device controller 25 accurately moving the disk 59 to control the angular orientation of the fiber and accurately moving the disk 61 to control the longitudinal position of the fiber. The longitudinal position is of course obtained by moving the lead screw longitudinally which carries the end stop 45 longitudinally. The movements are independent so that the fiber can be rotated while held longitudinally stationary.

As the motor driving movement of the fiber is used while the magnet and the MRI system is in operation, it is essential that the motor and the associated control elements that are located within the room 11 are compatible with the MRI system. For this purpose, the power supply or control cable 24 and the motor must both be free from ferromagnetic components which would be responsive to the magnetic field. In addition it is necessary that the motor 22 and the cable 24 are both properly shielded against interference with the small radio frequency signals which must be detected for the MRI analysis to be effective.

As shown in FIG. 7, therefore, the room 11 is surrounded by a conductor which prevents penetration of radio frequency interference into the area within the room at the magnet. In addition the cable 24 and the motor 22 are surrounded by a conductor 80 which extends through an opening 81 in the conductor at the wall 11 through a cable port 82 within the wall 83 of the enclosure so that the whole of the motor and the cable are encased within the conductor 80 which is connected to the conductor within the wall. Thus the conductor 80 acts as a "worm hole" in the shielding thus retaining the motor 22 and the cable 24 effectively external to the shielding at the periphery of the room. The use of a Piezo-electric crystal to drive disks is particularly suitable and provides particular compatibility with the MRI system but other drive systems can also be used as set forth previously.

Figure 8:
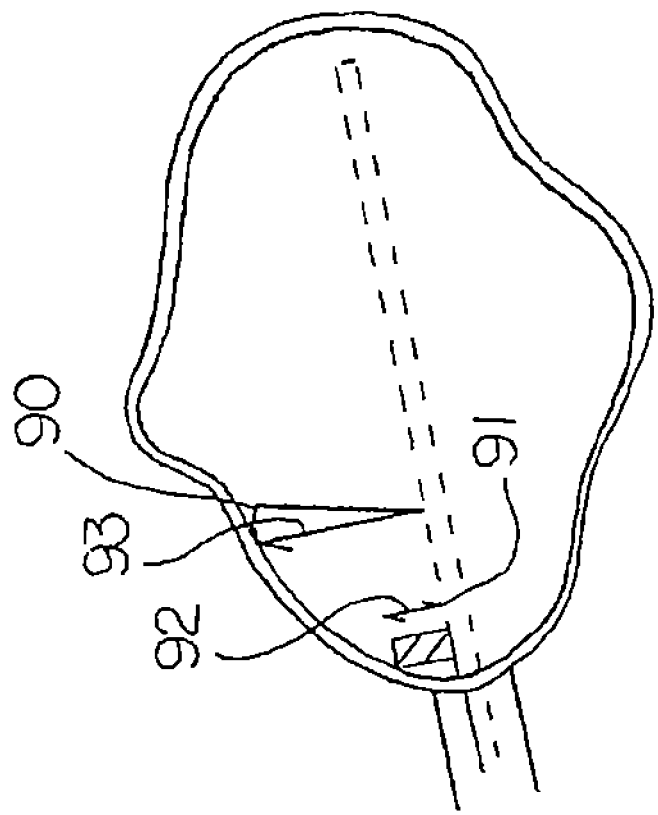
FIG. 8 is a schematic illustration of the effect of the apparatus on a tumour or other lesion to be coagulated.

In the method of operation, the patient is located on the patient table and so to be restrained so that the head of the patient is held fixed within the magnet to prevent motion artifacts. The MRI system is then operated in conventional manner to generate an image of the portion, generally a tumour, to be excised. The surgeon alone or in conjunction with suitable software available to one skilled in the art then analyses the images developed to locate the closed area surrounding the volume of the tumour and defining the external perimeter of the tumour as indicated at FIG. 8 at 90. The surgeon also determines the best route for directing the cannula to the tumour to avoid damaging intervening tissue and to provide a best course to the centre of the tumour which may be irregular in shape.

Having determined the course and direction of the cannula, the opening 34 is formed and the cannula inserted as previously described.

With the cannula in place, the motor is mounted on the frame and the frame adjusted to locate the motor so that the fiber can be inserted directly along the length of the cannula. With the motor properly aligned along the axis of the cannula, the fiber is inserted through the bore of the motor and into the cannula so as to extend through the cannula until the tip emerges just out of the outer end of the cannula. The distance of the motor from the cannula can be adjusted so that the tip just reaches the end of the cannula when the lead screw is fully retracted and the end stop is located in place in the clamp 72.

With the motor and fiber thus assembled, the MRI system is arranged to carry out experiments which generate temperature measurements in the boundary zone 90. The temperature is detected over the full surface area of the boundary rather than simply at a number of discrete locations. While the experiments to detect the temperature are continued, the fiber is moved longitudinally to commence operation at a first position just inside the volume of the tumour. At a selected angular orientation of the beam, pulses of radiation are emitted by the laser and transmitted into the tumour through the beam 37. The pulses are continued while the temperature in the boundary layer 90 is detected. As the pulses supply heat energy into the volume of the tumour, the tumour is heated locally basically in the segment shaped zone defined by the beam but also heat is conducted out of the volume of the beam into the remainder of the tumour at a rate dependant upon the characteristics of the tumour itself. Heating at a localised area defined by the beam is therefore continued until the heat at the boundary layer 90 is raised to the predetermined coagulation temperature of the order of 55 to 65° C. Once the boundary layer reaches this temperature, heating at that segment shaped zone within the disk is discontinued and the fiber is moved either longitudinally to another disk or angularly to another segment or both to move to the next segment shaped zone of the tumour to be heated. It is not necessary to predict the required number of pulses in advance since the detection of temperature at the boundary is done in real time and sufficiently quickly to prevent overshoot. However, predictions can be made in some circumstances in order to carry out the application of the heat energy as quickly as possible by applying high power initially and reducing the power after a period of time.

It is of course desirable to effect heating as quickly as possible so as to minimize the operation duration. For this purpose the number of pulses per second, or power of the heat source, may also be varied based upon the above predication depending upon the characteristics of the tumour as detected in the initial analysis. Thus the system may vary the energy pulse rate or power-time history of the heat source to modify the penetration depth of the heat induced lesion so that it can control the heating zone of an irregularly shaped lesion.

However the energy application rate cannot be so high that the temperature rises too quickly so that over shooting of the desired temperature at the boundary occurs with the possibility of damage to tissue outside the boundary. The rate of energy application is therefore selected depending upon the size and consistency of the tumour to effect heating at a controlled rate in order to achieve the required temperature at the boundary without the possibility of over shoot. The rate of heat application can also be varied in dependence upon the distance of the boundary from the axis of the fiber. Thus the axis of the fiber is indicated at 91 in FIG. 8 and a first distance 92 of the beam to the boundary is relatively short at the entry point of the fiber into the tumour and increases to a second larger distance 93 toward the center of the tumour. In addition to pulses per second, it is also possible to adjust the power-time history of the laser energy to maximize penetration into the lesion. That is to use high power first for a short period of time and then ramp the power down throughout the duration of the treatment at that particular location.

In some cases it is desirable to maintain the fiber stationary at a first selected longitudinal position and at a first selected angular orientation until the temperature at the boundary reaches the required temperature. In this case the fiber is then rotated through an angle approximately equal to the beam angle to commence heating at a second angular orientation with the fiber being rotated to a next angular orientation only when heating at that second orientation is complete. In this way heating is effected at each position and then the fiber rotated to a next orientation position until all angular orientations are completed.

After a first disk shaped portion of the tumour is thus heated, the fiber is moved longitudinally through a distance dependent upon the diameter of the tumour at that location and dependant upon the beam angle so as to ensure the next disk shaped volume of tumour heated contains all of the tumour structure without intervening localised portions of the tumour which are not heated to the required temperature. Thus the fiber is moved longitudinally in steps which may vary in distance depending upon the diameter and structure of the tumour as determined by the initial analysis. However the total heating of the tumour is preferably determined by the temperature at the boundary without the necessity for analysis of the temperatures of the tumour inside the boundary or any calculations of temperature gradients within the tumour.

When the complete boundary of the tumour has been heated to the predetermined coagulation temperature, the treatment is complete and the apparatus is disassembled for removal of the fiber and the cannula from the patient.

The system allows direct and accurate control of the heating by controlling the temperature at the surface area defined by the boundary of the tumour so that the whole of the volume of the tumour is properly heated to the required temperature without the danger of heating areas external to the tumour beyond the coagulation temperature.

In order to maximize the amount of heat energy which can be applied through the fiber and thereby to effect treatment of larger tumors, it is highly desirable to effect cooling of the tissue immediately surrounding the end of the fiber so as to avoid overheating that portion of the tissue. Overheating beyond the coagulation temperature is unacceptable since it will cause carbonization which will inhibit further transmission of the heat energy. Thus without the cooling it is generally necessary to limit the amount of heat energy which is applied. As energy dissipates within the tissue, such a limitation in the rate of application of energy limits the size of the tumor to be treated since dissipation of energy prevents the outside portions of the tumor from being heated to the required coagulation temperature.

In FIGS. 9 and 10 is therefore shown a modified laser probe which can be used in replacement for the probe previously described, bearing in mind that it is of increased diameter and thus minor modifications to the dimensions of the structure are necessary to accommodate the modified probe.

The modified probe 100 comprises a fiber 101 which extends from a tip portion 102 including the light dispersion arrangement previously described to a suitable light source at an opposed end of the fiber as previously described. The probe further comprises a support tube 103 in the form of a multi-lumen extruded plastics catheter for the fiber which extends along the fiber from an end 104 of the tube just short of the tip 102 through to a position beyond the fiber drive system previously described. The tube 103 thus includes a cylindrical duct 104 extending through the tube and there are also provided two further ducts 105 and 106 parallel to the first duct and arranged within a cylindrical outer surface 107 of the tube.

The supporting tube 103 has at its end opposite the outer end 104 a coupling 108 which is molded onto the end 109 and connects individual supply tubes 110, 111 and 112 each connected to a respective one of the ducts 104, 105 and 106.

Multi-lumen catheters of this type is commercially available and can be extruded from suitable material to provide the required dimensions and physical characteristics. Thus the duct 104 is dimensioned to closely receive the outside diameter of the fiber so that the fiber can be fed through the duct tube 110 into the duct 104 and can slide through the support tube until the tip 102 is exposed at the end 104.

While tubing may be available which provides the required dimensions and rigidity, in many cases, the tubing is however flexible so that it bends side to side and also will torsionally twist. The support tube is therefore mounted within an optional stiffening tube or sleeve 114 which extends from an end 115 remote from the tip 102 to a second end 106 adjacent to the tip 102. The end 116 is however spaced rearwardly from the end 104 of the tubing 103 which in turn is spaced from the tip 102. The distance from the end 106 to the tip 102 is arranged to be less than a length of the order of 1 inch. The stiffening tube 114 is formed of a suitable stiff material which is non-ferro-magnetic so that it is MRI compatible. The support tube 103 is bonded within the stiffening tube 114 so that it cannot rotate within the stiffening tube and cannot move side to side within the stiffening tube. The stiffening tube is preferably manufactured from titanium, ceramic or other material which can accommodate the magnetic fields of MRI. Titanium generates an artifact within the MRI image. For this reason the end 116 is spaced as far as possible from the tip 102 so that the artifact is removed from the tip to allow proper imagining of the tissues.

At the end 116 of the stiffening tube 114 is provided a capsule 120 in the form of a sleeve 121 and domed or pointed end 122. The sleeve surrounds the end 116 of the stiffening tube and is bonded thereto so as to provide a sealed enclosure around the exposed part of the tube 103. The capsule 120 is formed of quartz crystal so as to be transparent to allow the escape of the disbursed light energy from the tip 102. The distance of the end of the stiffening tube from the tip is arranged such that the required length of the capsule does not exceed what can be reasonably manufactured in the transparent material required.

The tube 111 is connected to a supply 125 of a cooling fluid and the tube 112 is connected to a return collection 126 for the cooling fluid. Thus the cooling fluid is pumped through the duct 105 and escapes from the end 104 of the tube 103 into the capsule and then is returned through the duct 106. The cooling fluid can simply be liquid nitrogen which is allowed to expand to nitrogen gas at cryogenic temperatures which is then pumped under the pressure in the gas through the duct 105 and returns through the duct 106 where it can be simply released to atmosphere at the return 126.

In an alternative arrangement the supply 125 and the return 126 form parts of a refrigeration cycle where a suitable coolant is compressed and condensed at the supply end and is evaporated at the cooling zone at the capsule 120 so as to transfer heat from the tissue surrounding the capsule 120 to the cooling section at the supply end.

The arrangement set forth above allows the effective supply of the cooling fluid in gaseous or liquid form through the ducts 105 and 106 and also effectively supports the fiber 101 so that it is held against side to side or rotational movement relative to the stiffening tube 114. The location of the tip 102 of the fiber is therefore closely controlled relative to the stiffening tube and the stiffening tube is driven by couplings 130 and 131 shown schematically in FIG. 9 but of the type described above driven by reciprocating motor arrangements as set forth hereinbefore.

In FIGS. 11 and 12 is shown the tip section of an alternative probe in which cooling of the tip section is effected using expansion of a gas into an expansion zone. The tip only is shown as the remainder of the probe and its movement are substantially as previously described.

Thus the probe comprises a rigid extruded tube 200 of a suitable material for example titanium which is compatible with MRI (non-ferromagnetic) and suitable for invasive medical treatment. A further smaller cooling fluid supply tube 202 is also separately formed by extrusion and is attached by adhesive to the inside surface of the outer tube. An optical fiber 204 is also attached by adhesive to the inside surface the outer tube so that the fiber is preferably diametrically opposed to the tube 202.

The tube 202 is swaged at its end as indicated at 205, which projects beyond the end of the tube 201, to form a neck section of reduced diameter at the immediate end of the tube 202. Thus in manufacture the extruded tube 201 is cut to length so as to define a tip end 207 at which the outer tube terminates in a radial plane. At the tip end beyond the radial plane, the outer of the inner tube 202 is swaged by a suitable tool so as to form the neck section 205 having an internal diameter of the order of 0.003 to 0.005 inch.

The fiber 204 is attached to the tube 201 so that a tip portion 208 of the fiber 204 projects beyond the end 207 to a chamfered end face 209 of the fiber which is cut at 450 to define a reflective end plane of the fiber.

The end 207 is covered and encased by a molded quartz end cap 210 which includes a sleeve portion 211 closely surrounding the last part of the tube 200 and extending beyond the end 207 to an end face 212 which closes the capsule. The end face 212 is tapered to define a nose 213 which allows the insertion of the probe to a required location as previously described. The end of the tube 201 may be reduced in diameter so that the capsule has an outer diameter matching that of the main portion of the tube. However in the arrangement shown the capsule is formed on the outer surface so that its outer diameter is larger than that of the tube and its inner diameter is equal to the outer diameter of the tube.

A thermocouple 214 is attached to the inside surface of the outer tube 200 at the end 207 and includes connecting wires 215 which extend from the thermocouple to the control unit schematically indicated at 226. Thus the thermocouple provides a sensor to generate an indication of the temperature at the end 207 within the quartz capsule. The quartz capsule is welded to or bonded to the outer surface of the tube as indicated at 215 so as to form a closed expansion chamber within the quartz capsule beyond the end 207. The inner surface 216 of the quartz capsule is of the same diameter as the outer surface of the tube 200 so that the expansion chamber beyond the end of the tube 200 has the same exterior dimension as the tube 200.

The quartz capsule is transparent so as to allow the reflected beam of the laser light from the end face 209 of the fiber to escape through the transparent capsule in the limited angular direction substantially at right angles to the longitudinal axis of the fiber and within the axial plane defined by that longitudinal axis.

The tube 202 is connected at its end opposite to the tip to a fluid supply 219 which forms a pressurized supply of a suitable cooling fluid such as carbon dioxide or nitrous oxide. The fluid supply 219 is controlled by the control unit 216 to generate a predetermined pressure within the fluid supply to the tube 202 which can be varied so as to vary the flow rate of the fluid through the neck 205. The fluid is supplied at normal or room temperature without cooling. The fluid is normally a gas at this pressure and temperature but fluids which are liquid can also be used provided that they form a gas at the pressures within the expansion chamber and thus go through an adiabatic gas expansion through the restricted orifice into the expansion chamber to provide the cooling effect.

Thus the restricted orifice has a cross-sectional area very much less than that of the expansion chamber and the return duct provided by the inside of the tube 201. The items that reduce the effective cross sectional area of the return tube 201 are the optical fibre, the supply tube, two thermocouple wires, the shrink tube that fixes the thermocouple wires to the optical fibre and the adhesives used to bond the items into place (at the inlet of the discharge duct). Without the area of the adhesives included in the calculation, the exhaust duct area is about 300 times larger than a delivery orifice diameter of 0.004" (the target size). When considering the area occupied by the adhesives, the exhaust duct inlet area would be approximately 200 to 250 times larger than the 0.004" diameter orifice. Considering the manufacturing tolerance range of the supply tube orifice diameter alone, the exhaust duct area could be anywhere between 190 to 540 times larger than the orifice area (without considering the area occupied by adhesives). It is our estimation that a 200/1 gas expansion will be required to achieve appropriate cooling.

This allows the gas as it passes into the expansion chamber beyond the end 205 to expand as a gas thus cooling the quartz capsule and the interior thereof at the expansion chamber to a temperature in the range minus 20° C. to zero ° C. This range has been found to be suitable to provide the required level of cooling to the surface of the quartz capsule so as to extract heat from the surrounding tissue at a required rate. Variations in the temperature in the above range can be achieved by varying the pressure from the supply 219 so that in one example the pressure would be of the order of 700 to 850 psi at a flow rate of the order of 5 liters per min.

The tube 202 has an outside diameter of the order of 0.014 inch OD, the tube 203 has a diameter of the order of 0.079 inch. Thus a discharge duct for the gas from the expansion chamber is defined by the inside surface of the tube 200 having a flow area which is defined by the area of the tube 200 minus the area taken up by the tube 202 and the fiber 207. This allows discharge of the gas from the expansion chamber defined within the quartz capsule at a pressure of the order of 50 psi so that the gas can be simply discharged to atmosphere if inert or can be discharged to an extraction system or can be collected for cooling and returned to the fluid supply 219 if economically desirable. Tip cooling is necessary for optimum tissue penetration of the laser or heating energy, reduction of tissue charring and definition of the shape of the coagulated zone. The gas expansion used in the present invention provides an arrangement which is suitable for higher power densities required in this device to accommodate the energy supplied by the laser heating system.

The tip 208 of the fiber 204 is accurately located within the expansion zone since it is maintained in fixed position within the quartz capsule by its attachment to the inside surface of the outer tube. The fiber is located forwardly of the end 207 sufficiently that the MRI artifact generated by the end 207 is sufficiently removed from the plane of the fiber end to avoid difficulties in monitoring the temperature within the plane of the fiber end. The outlet orifice of the tube 202 is also located forwardly of the end 207 so as to be located with the cooling effect generated thereby at the plane of the fiber end.

The end face 209 is located within the expansion chamber 216 so that it is surrounded by the gas with no liquid within the expansion chamber. Thus in practice there is no condensate on the end face 209 nor any other liquid materials within the expansion chamber which would otherwise interfere with the reflective characteristics of the end face 209.

The end face 209 is coated with a reflective coating such as a dual dielectric film. This provides a reflection at two required wave lengths of the laser light which are used as a visible guide beam and as the heat energy source such as He—Ne and Nd:YAG respectively. An alternative coating is gold which can alone provide the reflections at the two wavelengths.

The arrangement of the present invention provides excellent MRI compatibility both for anatomic imaging as well as MR thermal profiling.

In operation, the temperature within the expansion zone is monitored by the sensor 214 so as to maintain that temperature at a predetermined temperature level in relation to the amount of heat energy supplied through the fiber 204. Thus the pressure within the fluid supply is varied to maintain the temperature at that predetermined set level during the hyperthermic process.

As described previously, the probe is moved to an axial location within the volume to be treated and the probe is rotated in steps so as to turn the heating zone generated by the beam B into each of a plurality of segments within the disk or radial plane surrounding the end face 209. Within each segment of the radial plane, heat energy is supplied by the beam B which is transmitted through the quartz capsule into the tissue at that segment. The heat energy is dissipated from that segment both by reflection of the light energy into adjacent tissue and by conduction of heat from the heated tissue to surrounding tissue.

The surface of the capsule is cooled to a temperature so that it acts to extract heat from the surrounding tissue at a rate approximately equal to the dissipation or transfer of heat from the segment into the surrounding tissue. Thus the net result of the heating effect is that the segment alone is heated and surrounding tissue not in the segment required to be heated is maintained without any effective heating thereon, that is no heating to a temperature which causes coagulation or which could otherwise interfere with the transmission of heat when it comes time to heat that tissue in another of the segments. In this way when a first segment is heated to the required hyperthermic temperature throughout its extent from the probe to the peripheral surface of the volume, the remaining tissues in the areas surrounding the probe are effectively unheated so that no charring or coagulation has occurred which would otherwise prevent dissipation of heat and in extreme cases completely prevent penetration of the beam B.

Thus when each segment in turn has been heated, the probe can be rotated to the next segment or to another segment within the same radial plane and further heating can be effected of that segment only.

In practice in one example, the laser energy can be of the order of 12 to 15 watts penetrating into a segment having an angle of the order of 60 to 80 degrees to a depth of the order of 1.5 cms. In order to achieve this penetration without causing heating to the remaining portions of the tissue not in the segment, cooling of the outside of the capsule to a temperature of the order of minus 5° C. is required.

Figure 13:
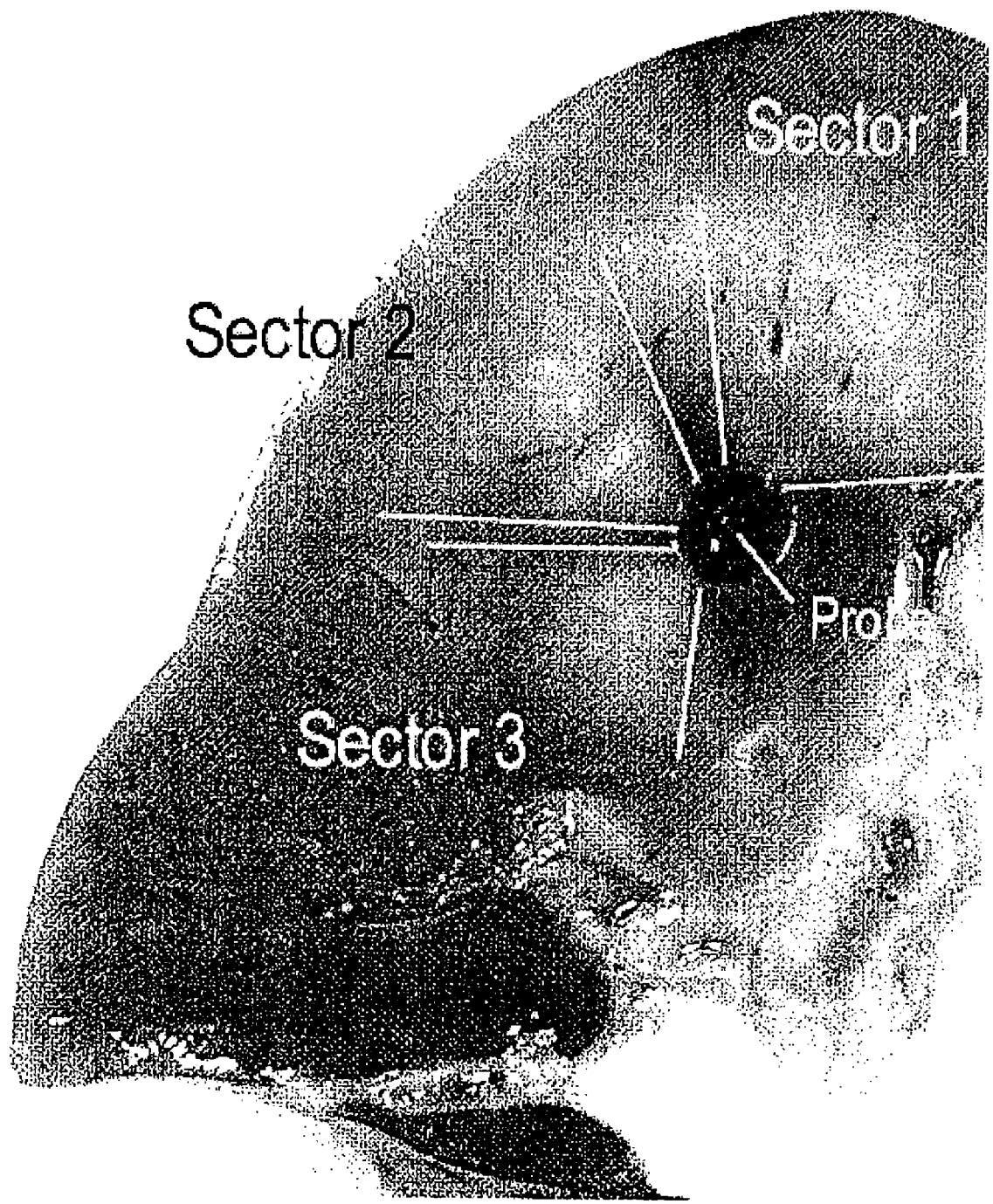
FIG. 13 is a photograph of a cross section of a tissue sample which has been heated in three separate segments showing the absence of heating outside the segments.

In FIG. 13 is shown an actual example of a cross-section of tissue which has been heated in three separate segments marked as sectors 1, 2 and 3. The central dark area is where the probe was located before it was removed to allow the cross-sectional slice to be taken. The darker area which forms approximately 100 degrees opposite sector 2 indicates that no heating has been applied to that area. The lighter color in the sectors 1, 2 and 3 indicates coagulation of the tissue. Similarly it will be noted that the tissue is of the darker color (not heated) in the smaller areas between sectors 2 and 3 and between sectors 1 and 2. Thus the cooling effect of the present invention achieves the effect required of limiting or prevention heating to the areas outside the selected segments.

The tube 200 is in the example shown above of a rigid structure for insertion in a straight line as previously described into a specific location. The use of a rigid material such as titanium for the outer tube avoids the necessity for the cannula previously described and allows the alignment of the probe in its mounting and drive arrangement as previously described to the required location in the patient without previously setting up a cannula. However other arrangements can be provided in which the tube 200 is formed of a fully or partial flexible material allowing the tube 200 to bend so as to allow insertion along suitable passageways such as veins or arteries within the patient by using guiding systems well known to one skilled in the art.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

To obtain proper paragraph numbering after paragraph 99, use Heading 2 for the appropriate style.

What is claimed is:

1. A probe for use in effecting treatment in a patient comprising:
    an imaging control system arranged to record an identified volume in the patient the whole of which volume is to be heated to a required temperature, the volume being defined by a peripheral surface of the volume;
    a heating system for applying heat to the volume within the patient including:
        a heat source;
        a probe having a longitudinal axis and an end with the heat source carried thereon;
        a drive system for inserting the end of the probe into the volume and for rotating the probe about its axis;
        the probe being arranged to cause directing of heat from the end in a direction at an angle to the longitudinal axis such that a heating effect of the probe lies in a disk surrounding the axis;
        the probe being arranged such that the direction of the heat defines a heating zone which forms a limited angular orientation of heating within the disk such that, as the probe is rotated, the probe causes heating of different angular segments of the volume within the disk;
        the probe being arranged such that the application of heat by the probe to a selected angular segment causes heat to be transferred from the selected angular segment into parts of the volume outside the selected angular segment surrounding the end of the probe;
        a cooling system for applying cooling to the end of the probe so as to extract heat from parts surrounding the probe by conduction of heat therefrom;
        and a control system for controlling the heating system and the cooling system;
    the cooling system being arranged such that the amount of cooling applied to the probe relative to the amount of heating ensures that parts of the volume surrounding the end of the probe are cooled sufficiently to cause a net heating effect by which substantially only the selected angular segment of the heating zone is heated to the required temperature and parts outside the selected angular segment are not heated to the required temperature.

2. The probe of claim 1, wherein the drive system is automated.

3. The probe according to claim 1 wherein the probe comprises an outer tube and the supply duct is mounted within the outer tube with the end thereof including the necking extending beyond an end of the outer tube.

4. The probe according to claim 1 wherein the probe comprises an outer tube provided with a temperature sensor mounted on the inside surface of the outer tube at the end of the probe.

5. The probe according to claim 1 wherein the temperature of the probe is cooled to a temperature in the range of about zero to about minus 20 degrees Celsius.

6. The probe of claim 1 further including a supply duct for supplying the cooling fluid to the end of the probe.

7. The probe according to claim 6 wherein the cooling system includes a cooling fluid comprising a gas which is expanded through a restricting orifice.

8. The probe of claim 7 further including a return duct for the return of the expanded gas from the end of the probe.

9. The probe according to claim 8 wherein the return duct is of larger cross-sectional area than the supply duct.

10. The probe according to claim 9 wherein the return duct is of the order of 200 to 250 times larger than the supply duct.

11. The probe according to claim 8 wherein the probe comprises an outer tube, wherein the supply duct is arranged inside the outer tube and wherein the return duct is defined by an inside surface of the outer tube.

12. The probe according to claim 11 wherein the supply duct is attached to an inside surface of the outer tube.

13. The probe according to claim 11 wherein the outer tube includes a heat energy supply conduit for transporting the heat energy from a supply to the end of the probe and wherein the heat energy supply conduit is attached to the inside surface of the outer tube.

14. The probe according to claim 7 wherein the supply duct comprises a supply tube and the restricting orifice is formed by a reduced necking of the supply tube at an end thereof at the expansion zone.

15. The probe according to claim 7 wherein a temperature at the end of the probe is controlled by varying the pressure in the cooling fluid as supplied through the supply duct.

16. The probe according to claim 1 wherein the heat source comprises a laser, an optical fiber for communicating light from the laser, and a light directing element at an end of the fiber, wherein the light directing element comprises a chamfered end of the fiber and wherein the chamfered end is located in the gas in the expansion zone.

17. The probe according to claim 16 wherein the chamfered end is arranged at 45 degrees.

18. The probe according to claim 16 wherein the chamfered end carries a coating arranged to reflect light at two different wavelengths.

19. The probe according to claim 16 wherein there is provided a temperature sensor at the end of the probe.

20. The probe according to claim 16 wherein the probe further includes an outer tube and a transparent capsule enclosing an end of the outer tube with the fiber extending to a position beyond the end of the outer tube into the capsule.

* * * * *